(12) United States Patent
Liu et al.

(10) Patent No.: US 9,541,488 B2
(45) Date of Patent: Jan. 10, 2017

(54) PARTICLE SAMPLING AND MEASUREMENT IN THE AMBIENT AIR

(71) Applicant: MSP Corporation, Shoreview, MN (US)

(72) Inventors: Benjamin Y. H. Liu, North Oaks, MN (US); Virgil A. Marple, Maple Plain, MN (US); Francisco Romay, Vadnais Heights, MN (US); Lin Li, Shoreview, MN (US)

(73) Assignee: MSP CORPORATION, Shoreview, MN (US)

( * ) Notice: Subject to any disclaimer, the term of this patent is extended or adjusted under 35 U.S.C. 154(b) by 0 days.

(21) Appl. No.: 14/031,661

(22) Filed: Sep. 19, 2013

(65) Prior Publication Data
US 2014/0083167 A1 Mar. 27, 2014

Related U.S. Application Data

(60) Provisional application No. 61/704,148, filed on Sep. 21, 2012.

(51) Int. Cl.
G01N 15/06 (2006.01)
G01N 1/22 (2006.01)
G01N 5/02 (2006.01)

(52) U.S. Cl.
CPC ............ *G01N 15/06* (2013.01); *G01N 1/2205* (2013.01); *G01N 5/02* (2013.01); *G01N 15/0606* (2013.01)

(58) Field of Classification Search
CPC .................. G01N 15/06; G01N 1/2202; G01N 2001/2223
USPC .............. 73/23.2, 28.01, 28.02, 28.04, 28.05
See application file for complete search history.

(56) References Cited

U.S. PATENT DOCUMENTS

| | | | |
|---|---|---|---|
| 5,553,507 A * | 9/1996 | Basch et al. ............... 73/863.01 |
| 7,597,015 B2 * | 10/2009 | Harley ......................... 73/865.5 |
| 2002/0122177 A1 * | 9/2002 | Sioutas et al. ................ 356/336 |
| 2002/0124632 A1 | 9/2002 | Reiter et al. |
| 2002/0178784 A1 * | 12/2002 | Radke et al. ................ 73/23.31 |
| 2004/0200265 A1 * | 10/2004 | Eden et al. .................. 73/23.31 |
| 2004/0259267 A1 | 12/2004 | Gundel et al. |
| 2005/0160792 A1 | 7/2005 | Booker |

(Continued)

FOREIGN PATENT DOCUMENTS

| | | |
|---|---|---|
| EP | 0799510 A2 | 6/1997 |
| GB | 2023831 A | 1/1980 |

(Continued)

OTHER PUBLICATIONS

Great Britain Search Report in corresponding Application No. GB1316822.4. Feb. 11, 2014.

*Primary Examiner* — Hezron E Williams
*Assistant Examiner* — David Z Huang
(74) *Attorney, Agent, or Firm* — Westman, Champlin & Koehler, P.A.; Z. Peter Sawicki; Amanda M. Prose

(57) ABSTRACT

An apparatus and method for sampling and measuring air born particulate matter includes an inlet for the particulate containing gas to enter. A mechanism then removes coarse particles larger than a selected size while permitting filtered particles of less than the selected size to pass through. A chamber containing a quartz crystal sensor permits the filtered particles that have passed through to deposit to create an output signal in response to the deposited particle mass.

14 Claims, 5 Drawing Sheets

(56) References Cited

U.S. PATENT DOCUMENTS

2005/0172735 A1    8/2005  Booker
2010/0129548 A1*  5/2010  Sneh .......................... 427/248.1

FOREIGN PATENT DOCUMENTS

WO      03002981 A1    1/2003
WO    2007062818 A1    6/2007

* cited by examiner

PARTICLE SAMPLING AND MEASUREMENT IN THE AMBIENT AIR

CROSS REFERENCE TO RELATED APPLICATION

The present application is based on and claims the benefit of U.S. provisional patent application Ser. No. 61/704,148, filed Sep. 21, 2012, the content of which is hereby incorporated by reference in its entirety.

BACKGROUND OF THE DISCLOSURE

Instruments for sampling and measuring particulate matter in air are useful for a variety of purposes. They can be used for scientific research to study the nature of a particulate air pollutant and its transport and dispersion in the ambient atmosphere. They are also useful for studying the effect of a particulate air pollutant on human health. In addition, such instruments can also be used for sampling and measuring airborne particulate matter for regulatory compliance purposes to determine if the ambient level is within safe limits prescribed by law.

SUMMARY OF THE DISCLOSURE

The present disclosure describes a method and an apparatus for sampling and measuring airborne particulate matter in the ambient atmosphere. The method and apparatus are particularly useful for compliance measurement purposes where ease of use and accuracy of measurement are most important.

The apparatus of this disclosure includes an inlet for particulate containing gas to enter. A mechanism then removes coarse particles larger than a selected size while permitting particles of less than the selected size to pass through. A chamber containing a quartz crystal sensor permits the particles that have passed through to deposit to create an output signal in response to the deposited particle mass.

The present disclosure also includes a method for measuring the concentration of particles in a gas using an apparatus in which the particulate containing gas enters into the chamber. The chamber contains a quartz crystal sensor on which particles deposit to create an output signal in response to the deposited particle mass. The chamber is maintained at a temperature sufficient to prevent vapor condensation on the sensor. The method includes removing coarse particles larger than about 10 μm in equivalent aerodynamic diameter permitting particles smaller than about 10 μm in equivalent aerodynamic diameter to pass through. Charging the particles of less than about 10 μm in equivalent aerodynamic diameter with ions generated in a corona discharge. Depositing the passed through particles on the quartz crystal sensor and measuring the output signal of the quartz crystal sensor.

FIG. 5A and FIG. 5B are schematic diagrams of a quartz crystal micro-balance for sensing the deposited particle mass on the quartz crystal.

DESCRIPTION OF THE EMBODIMENTS

FIG. 1 illustrates a system for sampling and measuring airborne particles according to the present disclosure. The system, shown generally located at 100, has a sampling inlet 110 for ambient air carrying suspended particles to enter. The inlet 110 is provided with a particle separator to remove coarse particles larger than approximately 10 μm, thus allowing only smaller particles, i.e. those smaller than approximately 10 μm to flow through and reach the downstream components for sample collection and analysis.

One part of the air flowing along path 120 enters a sampling chamber 130 containing a filter 134 for collecting airborne particles on a filter for analysis, the rate of air flow along this path being maintained by a small electric pump 140. The flow rate of air is measured by a flow sensor and electronic controller 150. With the help of the electronic controller 150, which has feedback control, the flow rate can be maintained at a specific set-point value. The flow rate is typically less than about 30 liters per minute. Higher flow rates can be used. However a small amount of material is capable of being accurately analyzed for mass and/or chemical composition analysis using the apparatus and method described herein. It is unnecessary to use a high sampling flow rate to collect a large amount of material for analysis. A small and compact instrument as described herein is easy to setup and use in the laboratory or in the field, while providing the needed accuracy for the measurement. In comparison, traditional air samplers for environmental monitoring operate at a flow rate of approximately 40 cubic feet per minute, i.e. 1120 liters per minute. The 30 liter per minute flow rate described here is only approximately 2.5% of the traditional flow rate used for this purpose.

Another part of the airflow along path 160 enters a chamber 170 containing a particle mass sensing transducer 174 to monitor the mass of particles deposited on the sensing surface of the transducer 174. The airflow along this path is also maintained by a small pump 180, the flow rate being measured by a flow sensor and controller 190 to maintain the air flow at a specific set-point value.

A third part of the air flows along path 200 and enters another coarse particle separator 210 to remove coarse particles larger than approximately 2.5 or approximately 1.0 μm. After the coarse particle separator the air is divided into two downstream paths 220 and 230. Air path 220 leads to chamber 240 which contains a filter sampler collect airborne particle samples for analysis. The other air path 230 leads to chamber 250 which contains a transducer 254 for monitoring the mass of particles deposited on the transducer sensing surface for monitoring the mass concentration of airborne particles smaller than approximately 2.5 or approximately 1.0 μm in diameter.

Downstream of each of the chambers 240 and 250 are small electric pumps, 260 and 270 and flow sensors and controllers, 280 and 290, for controlling the rate of gas flow through the chambers 240 and 250 to their respective set-point values. The schematic diagram of the system located generally at 100 is therefore capable of collecting airborne particle samples in the PM10 and PM2.5 or PM1.0 size ranges for mass and/or chemical analyses, as well as providing airborne mass concentration values for PM10 and PM2.5, or PM10 and PM 1.0 determination. The terms PM10, PM 2.5 and PM1.0 particles are defined as atmospheric particulate matters from which particles larger than 10 μm, 2.5 μm or 1.0 μm in aerodynamic equivalent diameter have been removed. In the context of the present disclosure concerning method and apparatus for sampling and measuring atmospheric particulate matter, the term refers to a sample stream from which particles larger than the 10 μm, 2.5 μm or 1.0 μm in aerodynamic equivalent diameter have been removed.

Figure 1:
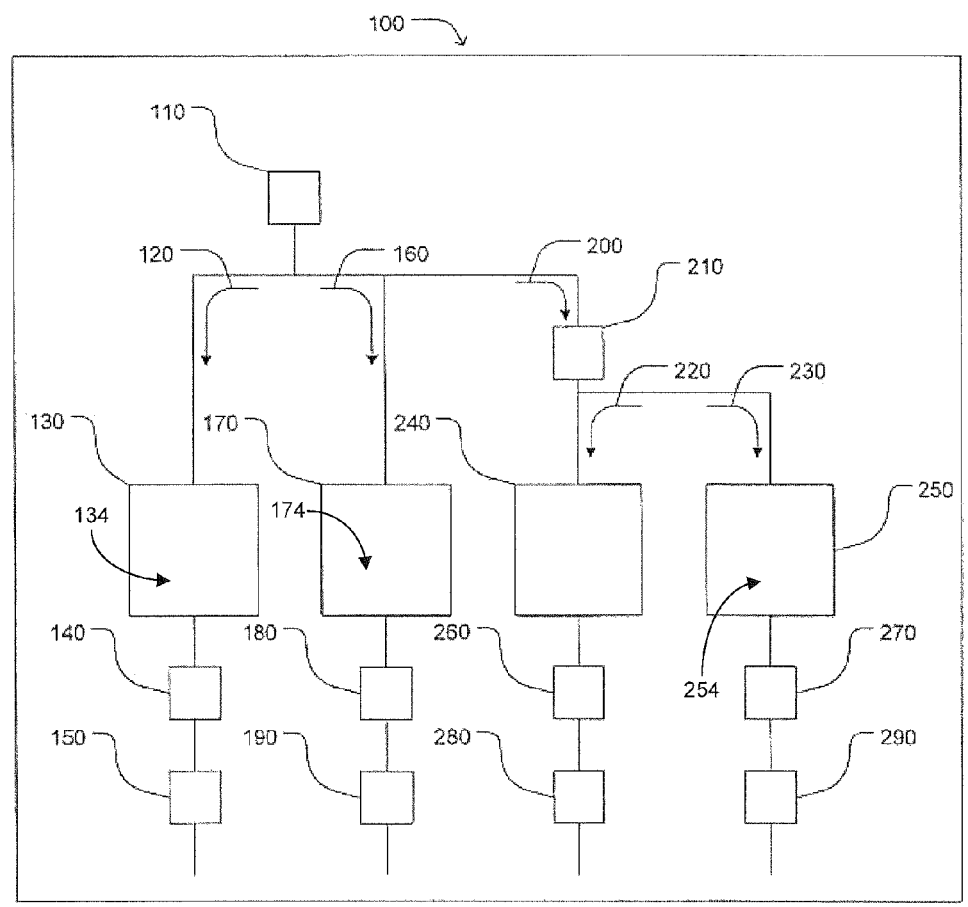
FIG. 1 is a schematic diagram of the system for sampling and measuring airborne particles in the ambient atmosphere in one preferred embodiment.
Figure 2:
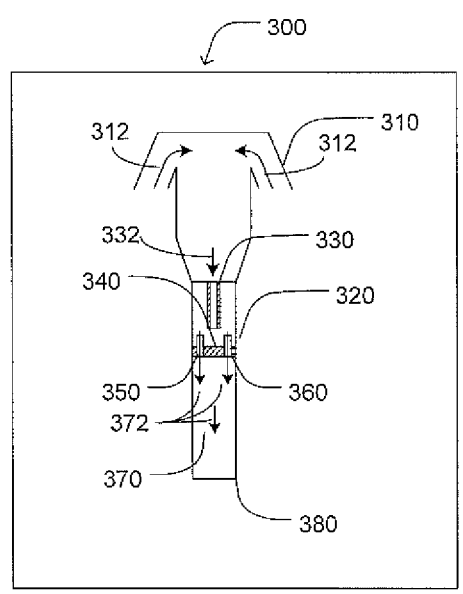
FIG. 2 is a schematic diagram of an inlet particle separator to remove particles larger than 10 μm in diameter.

FIG. 2 is a schematic diagram of the sampling inlet 110 of FIG. 1 being identified in FIG. 2 generally at 300, for sampling air from the ambient atmosphere. Air as indicated by arrows 312 is sampled into this inlet under cap 310. Located downstream of this sampling inlet is an inertial impactor (particle separator), shown generally located at 320. The impactor is provided with an inlet nozzle 330 to accelerate the airflow as indicated by arrow 332 to a high velocity. Large particles, because of their large size and their momentum, are impacted onto the impaction surface 340 and removed from the flowing air stream 332. The impactor is designed to remove particles that are larger than approximately 10 μm in aerodynamic equivalent diameters. Particles smaller than approximately 10 μm in aerodynamic equivalent diameter are carried by the air flow through flow tubes 350 and 360 into the downstream flow passageway 370 as indicated by arrows 372, and then exit the impactor through outlet 380.

The aerodynamic equivalent diameter of a particle is the diameter of a unit density sphere having the same settling speed as the particle in question. The concept of aerodynamic equivalent diameter and size separation by inertial impaction are well known to those skilled in the art in designing inertial particle separation devices and therefore will not be further discussed.

Figure 3:
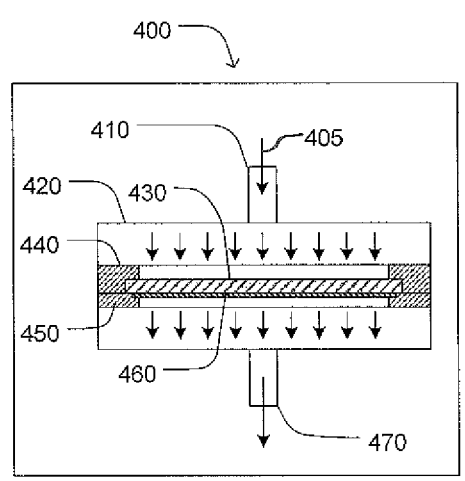
FIG. 3 is a schematic diagram of a filter sampler for collecting airborne particles for gravimetric or chemical analysis

FIG. 3 is a schematic diagram of a filter sampler for collecting airborne particles for gravimetric and/or chemical analysis. The filtration apparatus is shown generally located at 400. The filter sampler 400 is located in chambers 130 and 240 and was identified in FIG. 1. Air as indicated by arrow 405 is sampled through the inlet 410 of housing 420. The air, carrying suspended particles smaller than 10 μm in diameter, then flows through the filter 430 located inside. Filter 430 is clamped tightly between two metal pieces 440 and 450 to prevent flow leakage around the edges. The filter is supported on the downstream side by a rigid porous metal support 460. Alternatively, a rigid perforated metal plate can be used as the filter support. The filter is generally of circular, i.e. of a round shape, but other filter shapes such as a rectangle, or a square, can also be used.

The filter sampling apparatus of FIG. 3 is generally kept at a temperature that is near the ambient air temperature to make sure that the sizes of airborne particles, which may contain certain amount of water, are not greatly affected. Sometimes, the sampler may be operated at a few degrees Celsius above the ambient air temperature to prevent a large amount of water being present in the collected particle mass.

Figure 4:
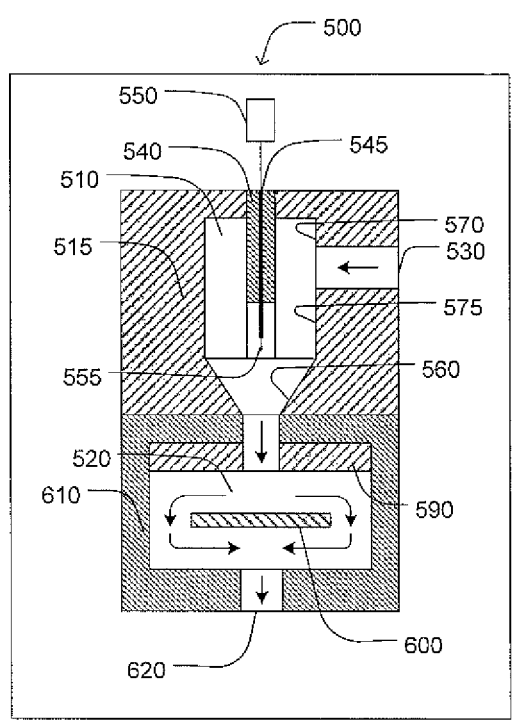
FIG. 4 is a sampler for depositing airborne particles onto a mass-sensing transducer in one preferred embodiment.

FIG. 4 illustrates an apparatus for charging airborne particles and depositing them on a quartz crystal microbalance for sensing the deposited particle mass. The apparatus is shown generally located at 500 and the apparatus 500 is located in chambers 170 and 250 and provided with two chambers. An upper chamber 510 is for charging the particles, while the lower chamber 520 functions as a particle precipitator to deposit the charged particles onto a mass-sending transducer for particle mass concentration determination.

The upper chamber 510 is constructed of a conducting material, such as stainless steel. Air, carrying particles smaller than about 10 μm in diameter, enter the chamber through inlet 530. Inside the chamber there is a needle 545 with a fine tip 555. The needle is embedded in an insulator 540 and connected to a source 550 of high DC voltage to create a corona discharge from the needle tip 555 to an inside conical surface 560 of the chamber. Most of the corona current is collected on the conical surface 560 inside the chamber. Surfaces that are farther away, such as 575 and 570, will have very little of the current collected there because of the much weaker electric field there. The high voltage source 550 is provided with electronic control circuitry in order to provide a stable voltage and/or current output to insure a high charging efficiency and repeatable performance characteristics.

The walls 610 of the lower chamber 520 are constructed of an insulating material, such as plastic or a ceramic. A metal electrode 590 is placed above the quartz crystal mass sensing transducer 600. The source of high voltage 550 is connected to electrode 590 while the quartz crystal transducer 600 is grounded. The high voltage source 550 is also provided with control circuitry (not shown) in order to vary the voltage to achieve optimal performance, while providing a repeatable voltage output to insure stable operation of the precipitator.

To prevent water vapor in air to condense on the transducer 600 both the upper and lower chambers of FIG. 4 are maintained at a suitably high temperature to prevent water vapor condensation in the chamber. A typical temperature is 40° C. A higher or a lower temperature can be used depending on the environmental conditions and the specific application of the apparatus.

Figure 5A:
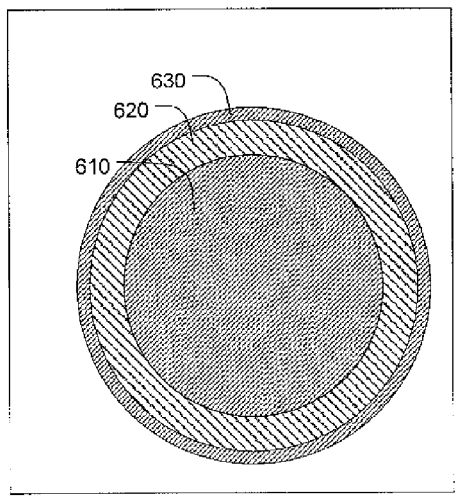
Figure 5B:
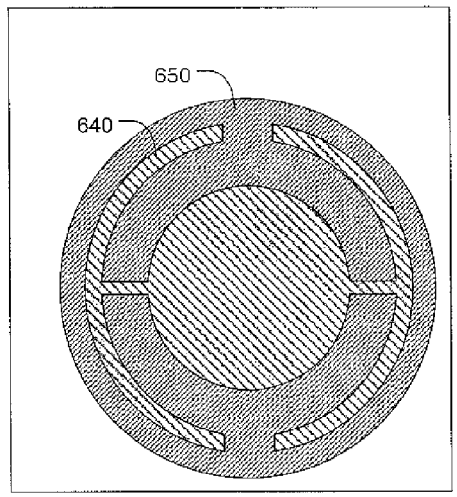

FIGS. 5a and 5b are schematic diagrams of a quartz crystal micro-balance for sensing the deposited particle mass on the quartz crystal. FIG. 5a shows the front side of the transducer while FIG. 5b shows its back side.

The mass sensing area 610 is on the front side of the transducer. Particles to be sensed are deposited in this area. The central area for mass sensing is surrounded by an annular electrode area 620 which is usually coated with a thin layer of gold. There is also an edge exclusive zone 630 where uncoated quartz is present. One suitable quartz is an AT cut crystal.

On the backside of the quartz crystal transducer, there is also a gold coated electrode 640 which is approximately the same diameter as the sensing zone on the front side. The uncoated quartz area is shown at 650. The transducer is set to vibrate at its resonant frequency by applying an excitation voltage to the electrodes. With the conventional AT cut quartz crystal used for mass sending, the vibration is in the transverse mode, i.e. in the direction parallel to the surface on which the particles are deposited. With deposited particle mass on the crystal surface, the resonant frequency of the crystal will become smaller compared to the resonant frequency when the crystal is clean. The change in frequency is thus proportional to the deposited particle mass, which can be used for particle mass determination.

The above description of the instrument has been described in terms of its use for airborne particle measurement. The same apparatus can also be used to measure particulate matter suspended in a gas media other than air. Particulate matter suspended in nitrogen, argon, and other inert gases may also contain suspended particles that need to be measured. The method and apparatus described herein are also suitable for such applications as well.

Although the present invention has been described with reference to preferred embodiments, workers skilled in the art will recognize that changes may be made in faun and detail without departing from the spirit and scope of the invention.

What is claimed is:

1. An apparatus for measuring particles in a gas, said apparatus comprising:
    an inlet for said gas to enter provided with a first mechanism to separate the gas into two or more flow paths, the mechanism configured to remove coarse particles larger than a first selected size and direct the gas with the coarse particles along a first flow path and permitting smaller particles of less than the first selected size to pass through the mechanism to a second flow path;
    a second mechanism to subsequently separate the gas along one of the two or more flow paths to remove coarse particles larger than a second, smaller selected size permitting gas flow with smaller particles of less than the second selected size to pass through, the second mechanism positioned downstream of the inlet;
    a first chamber containing a first quartz crystal sensor on which particles of less than one of the first or second selected size can deposit to create an output signal in response to a deposited particle mass, wherein said first chamber is maintained at a temperature sufficient to prevent vapor condensation on said first sensor; and
    a second chamber containing a second quartz crystal sensor and said second chamber for charging particles of less than the other of the first or second selected size with ions generated in a corona discharge and depositing the charged particles on the second quartz crystal sensor to generate an output signal in response to the deposited particle mass.

2. The apparatus of claim 1 said temperature being in the range from approximately 25° C. to approximately 55° C.

3. The apparatus of claim 1 said apparatus including a mechanism to maintain steady gas flow through said chamber.

4. The apparatus of claim 1 said apparatus including a gas filter for collecting a particle sample for analysis.

5. The apparatus of claim 4 said gas filter including a mechanism to maintain a steady gas flow through said filter.

6. The apparatus of claim 5 said mechanism to maintain a steady gas flow includes a variable speed pump, a flow sensor and an electronic controller.

7. The apparatus of claim 6 said steady gas flow through said filter being less than approximately 100 liters per minute.

8. The apparatus of claim 6 said gas flow through said chamber being at a temperature not higher than approximately 10° C. above the temperature of the gas entering the inlet.

9. The apparatus of claim 1, said coarse particles being removed by the first mechanism are larger than about 10 μin equivalent aerodynamic diameter.

10. The apparatus of claim 1, said second mechanism to remove coarse particles larger than approximately 2.5 μm or approximately 1.0 μm diameter.

11. A method for measuring concentration of particles in a gas using an apparatus having an inlet for the gas to enter, at least one chamber containing a first quartz crystal sensor on which particles deposit to create an output signal in response to a deposited particle mass, said chamber being maintained at a temperature sufficient to prevent vapor condensation on said first sensor, comprising the steps of:
    removing coarse particles larger than about 10 μm in equivalent aerodynamic diameter by separating the gas flow into one or more gas flows along two or more gas flow paths, at least one of the two or more gas flow paths permitting smaller particles of less than about 10 μm in equivalent aerodynamic diameter to pass through;
    removing coarse particles larger than approximately 2.5 μm or approximately 1.0 μm in aerodynamic equivalent diameter by further separating the gas flow into flows along two or more gas flow paths;
    charging the smaller particles with ions generated in a corona discharge;
    depositing the charged particles on said first quartz crystal sensor;
    measuring the output signal of said first quartz crystal sensor;
    charging the particles smaller than 2.5 μm or 1.0 μm particles in a second chamber containing a second quartz crystal sensor to produce second charged particles;
    depositing the second charged particles on said second quartz crystal sensor; and
    measuring the output signal of said second quartz crystal sensor to determine the deposited particle mass smaller than approximately 2.5 μm or approximately 1.0 μm in diameter.

12. The method of claim 11 said temperature being in the range from approximately 25° C. to approximately 55° C.

13. The method of claim 11 including a mechanism to maintain steady gas flow, said steady gas flow through said filter being less than approximately 100 liters per minute.

14. The method of claim 11 said gas flow through said chamber being at a temperature not higher than approximately 10° C. above the temperature of the gas entering the inlet.

* * * * *